United States Patent [19]
Scrivo et al.

[11] 3,986,854
[45] Oct. 19, 1976

[54] METHOD OF MAKING AUTOCLAVABLE INSTRUMENT WITH SINTERED FIBER GLASS ROD

[75] Inventors: Leonard Scrivo, Tuckahoe; James J. Lewis, Bronxville, both of N.Y.; Paul Binner, Dumont, N.J.

[73] Assignee: Vicon Products Corporation, Pelham Manor, N.Y.

[22] Filed: Sept. 23, 1974

[21] Appl. No.: 508,240

[52] U.S. Cl. .................................. 65/4 R; 65/1; 65/2; 65/DIG. 7; 128/11; 128/16; 128/397
[51] Int. Cl.² ................ C03C 23/20; C03B 37/00; A61B 1/06
[58] Field of Search ............ 65/DIG. 7, 2, 4 R, 4 A, 65/1; 128/11, 16, 397

[56] References Cited
UNITED STATES PATENTS

| | | | |
|---|---|---|---|
| 1,662,150 | 3/1928 | Kerr | 128/397 X |
| 3,091,235 | 5/1963 | Richards | 65/DIG. 7 |
| 3,327,712 | 6/1967 | Kaufman et al. | 65/DIG. 7 |
| 3,598,113 | 8/1971 | Moore | 128/11 |
| 3,766,909 | 10/1973 | Ozbey | 128/16 X |

*Primary Examiner*—S. Leon Bashore
*Assistant Examiner*—Frank W. Miga
*Attorney, Agent, or Firm*—Lerner, David, Littenberg & Samuel

[57] ABSTRACT

An autoclavable instrument, such as an autoclavable laryngoscope, is provided which includes fiber optics illuminating means and is especially adapted for medical and/or dental applications. The illuminating means includes an elongated sintered glass rod formed from an oriented fiber optics bundle comprising a plurality of glass fibers. The elongated glass rod may include curved or bent portions so as to conform to the contours of the instrument. A method is also provided for making an instrument as described above.

5 Claims, 6 Drawing Figures

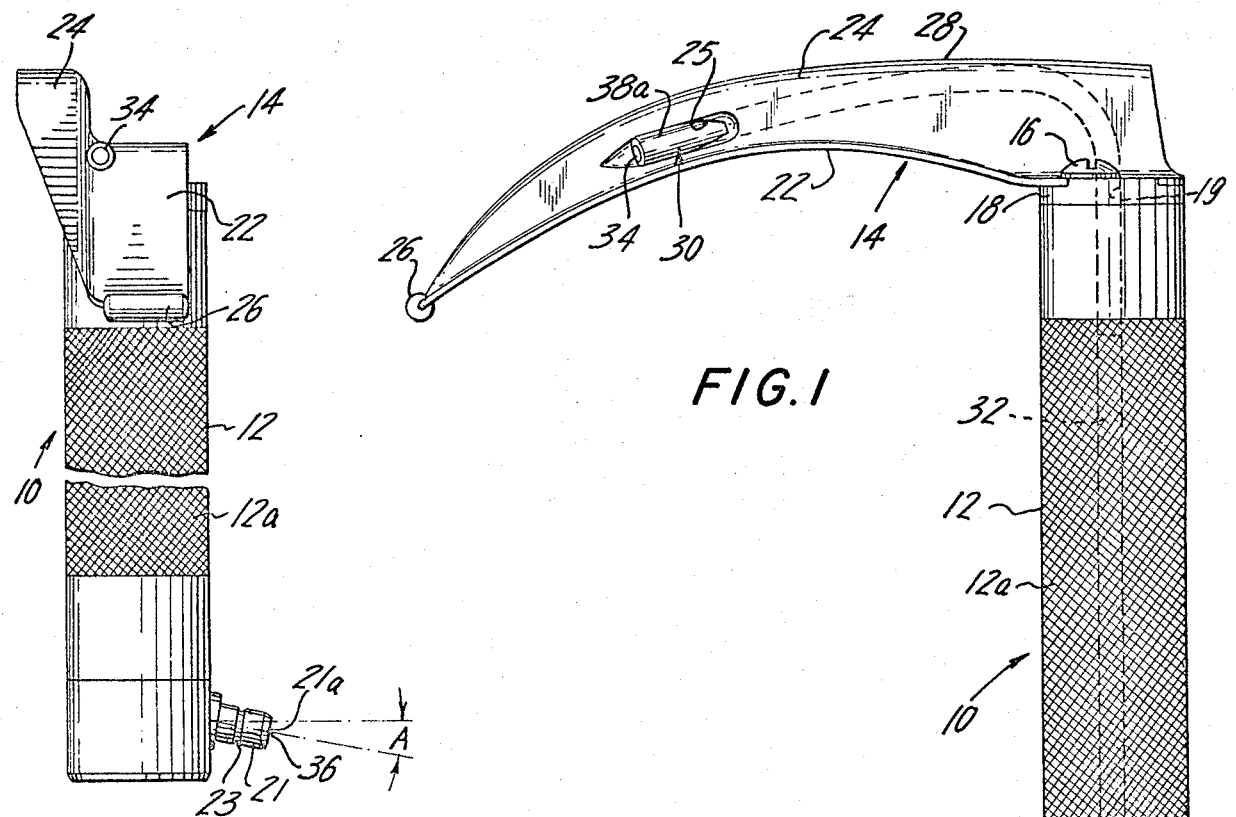
FIG.1
FIG.1A
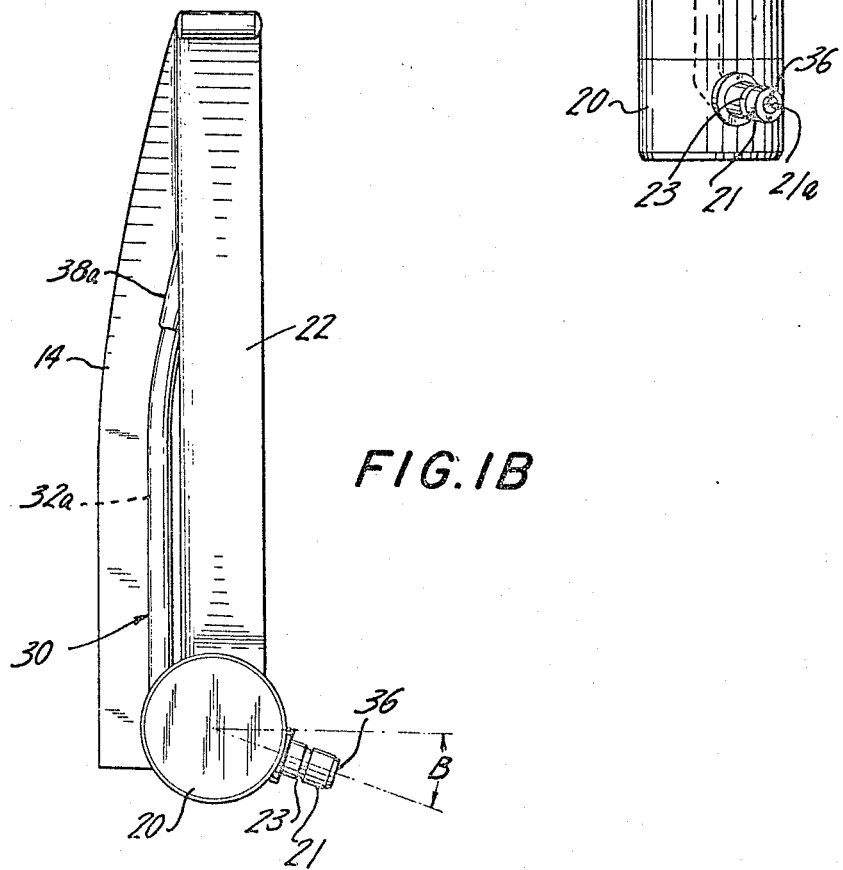
FIG.1B

METHOD OF MAKING AUTOCLAVABLE INSTRUMENT WITH SINTERED FIBER GLASS ROD

FIELD OF THE INVENTION

The present invention relates to autoclavable medical or dental instruments which include fiber optics elements as illuminating means therefor and a method for forming such instruments. In particular, the present invention is directed to autoclavable laryngoscopes.

BACKGROUND OF THE INVENTION

Conventional layrngoscopes usually consist of a chrome-plated brass blade employed as a tongue depressor to facilitate inspection of the pharynx and larynx or the insertion of anesthetic breathing tubes, which blade is pivotally and/or detachably connected to a hollow handle. Illumination is provided by a small light bulb or lamp mounted on a surface of the blade, the bulb being energized by batteries housed in the handle.

Adequate lighting in diagnostic and surgical procedures is an absolute must. However, the naked bulbs or lamps now employed in conventional laryngoscopes can hardly be said to provide the required illumination for such procedures. Firstly, bulbs now in use cause shadowing making remote areas difficult to observe. Secondly, such bulbs often do not have sufficient candle power to provide adequate illumination, especially for detailed examination of the larynx and trachea and to insure correct positioning of the tip of an endotracheal tube. Where it has been attempted to use higher intensity lamps in conjunction with line voltage rather than batteries to overcome the above drawbacks, it has been found that the heat generated by such lamps is excessive and the wire and currents around the patient could create a hazardous condition.

It has been suggested to employ bulbs or lamps similar to that now used in standard laryngoscopes in conjunction with a preformed bundle of individual light transmitting fibers in order to increase the intensity of light provided. Thus, for example, U.S. Pat. No. 3,598,113 to Moore discloses a disposable laryngoscope which includes a plastic blade connected to a hollow plastic handle unit that is disposable and a light unit that is not. The handle is adapted to receive with a free sliding fit a light unit which consists of a lamp, batteries and an operating switch in a cylindrical case. A preformed bundle of individual light transmitting optical fibers is carried by the blade and handle to conduct light from the light unit lamp within the handle to a point near the distal end of the blade.

U.S. Pat. No. 3,766,909 to Ozbey discloses a laryngoscope which includes a disposable blade and light guide. The blade is made of a relatively soft synthetic plastic and contains a relatively stiff light guide for transmitting light and for providing strength to the laryngoscope. The light guide is formed of light conducting rods or fibers formed of acrylic resin molded in a unitary bundle and curved to match the curvature of the blade. The handle portion of the Ozbey layrngoscope includes a hollow region containing dry-cell batteries and includes a mounting disk for supporting a socket and lightbulb within the hollow region.

Unfortunately, it has been found that the amount of illumination obtained from the lamp disposed in the Moore and Ozbey laryngoscopes is not entirely adequate and is, in fact, substantially less than that provided by a high intensity illumination source disposed remote to the laryngoscope.

Bundles of individual light transmitting optical fibers or filaments such as employed in U.S. Pat. No. 3,598,113 to Moore are normally preformed by securing individual fibers together in a bundle encapsulating both ends of such bundle in epoxy resin. It has been found that the epoxy resin employed for such purposes as well as the acrylic resin employed in the Ozbey patent will break down upon being subjected to high temperatures and pressures. Accordingly, a laryngoscope including a fiber optics bundle as described above in the Moore and Ozbey patents cannot be autoclaved (that is sterilized in moist heat under controlled pressure and temperature for a predetermined period) without causing damage to the fiber optics bundle. Thus, the laryngoscopes of these patents are limited to one time use.

BRIEF DESCRIPTION OF THE INVENTION

In accordance with the present invention, there is provided an autoclavable re-usable instrument which includes as illumination means therefor a fiber optics element which will not be damaged when subjected to standard autoclaving techniques. This is accomplished by employing a fiber optics element which is comprised of a sintered elongated glass rod formed from a plurality of glass fibers or filaments. The sintered elongated glass rod does not include epoxy or acrylic resin, or other materials which will be damaged during autoclaving.

In one aspect of the present invention, a method is provided for making an autoclavable instrument with a fiber optics element as illuminating means therefor, which includes the steps of providing a sintered elongated glass rod comprising a sintered oriented bundle formed from a plurality of glass fibers, the glass rod including first and second faces, and disposing the glass rod in a body portion of an autoclavable instrument with the first and second faces being externally disposed with respect to such body portion. The first and second faces may be polished to form first and second optical faces, such polishing step being performed before and after the glass rod is disposed in the body portion.

In a preferred embodiment of the above method, prior to disposing the glass rod in the body portion of the instrument, the glass rod is inserted in an autoclavable protective tubular member, such as a metallic tubular member. The glass rod is then disposed in the autoclavable instrument so that portions of the glass rod which are externally exposed with respect to such instrument, other than the optical faces thereof, are protected by such protective tubular member.

The glass rod including the protective tubular member may be shaped or bent so as to follow the contours of the autoclavable instrument. The shaping or bending operation required to shape the glass rod and its protective tubular member comprises heating at least a portion of the glass rod protected by the protective tubular member to a temperature sufficiently high to soften such portion of said glass rod and protective tubular member disposed thereon, bending the glass rod and protective tubular member into a predetermined desired shape to fit the shape of the particular instrument, and cooling the glass rod and protective member, such as, by subjecting the same to ambient air.

It will be appreciated that the above method may be employed for making many types of autoclavable medical and dental instruments which include a fiber optics element as a source of illumination therefor such as laryngoscopes, endoscopes, dental handpieces, boroscopes, mirrors and the like.

As a further aspect of the present invention there is provided an autoclavable instrument adapted for medical or dental applications which includes an autoclavable working body portion and autoclavable illuminating means therefor. The illuminating means takes the form of the sintered elongated glass rod described above. Such sintered elongated glass rod will have first and second optical faces, the first optical face being disposed on the working portion of the instrument to provide illumination therefor and the second optical face is adapted to be connected to a second fiber optics bundle adapted to be operatively connected up with a light source which preferably is in the form of a high intensity remote illuminator which includes a high intensity quartz halogen projection lamp such as a DNF lamp (21 volts, 3450° K color temperature) or DNE lamp (120 volts, 3350° K color temperature). so as to provide a complete light path from the first optical face to the light source.

In a preferred embodiment of the above-described autoclavable instrument, a rigid protective tubular member, such as a metallic tubular member, is disposed about and encloses at least a portion of the glass rod, and especially those portions of the glass rod which are externally exposed to the instrument.

The method of the invention is particularly adapted for making an autoclavable layrngoscope which includes a handle portion, a forwardly extending blade portion connected to one end of the handle portion at substantially right angular relation thereto, and illuminating means operatively associated with the handle portion and the blade portion. The illuminating means comprises an elongated sintered glass rod as described above having first and second optical faces and formed from an oriented fiber optics bundle comprised of a plurality of glass fibers. The first optical face and a first section of the glass rod is connected to the blade portion. The glass rod includes a second section which includes a curved portion which extends from the blade portion and follows the contours of juncture between the handle portion and the blade portion and extends into the handle portion. The glass rod also includes a third section which extends through the handle portion and terminates in the second optical face. The second optical face is adapted to be connected to a second fiber optics bundle which is adapted to be operatively connected up with a light source so as to complete a light path from the first optical face to the light source.

DESCRIPTION OF THE FIGURES

FIG. 1 is a side elevational view of a preferred autoclavable laryngoscope in accordance with the present invention;

FIG. 1A is a front view of a portion of the autoclavable laryngoscope shown in FIG. 1;

FIG. 1B is a bottom view of a portion of the autoclavable laryngoscope shown in FIG. 1;

DETAILED DESCRIPTION OF PREFERRED EMBODIMENTS

Figure 2:
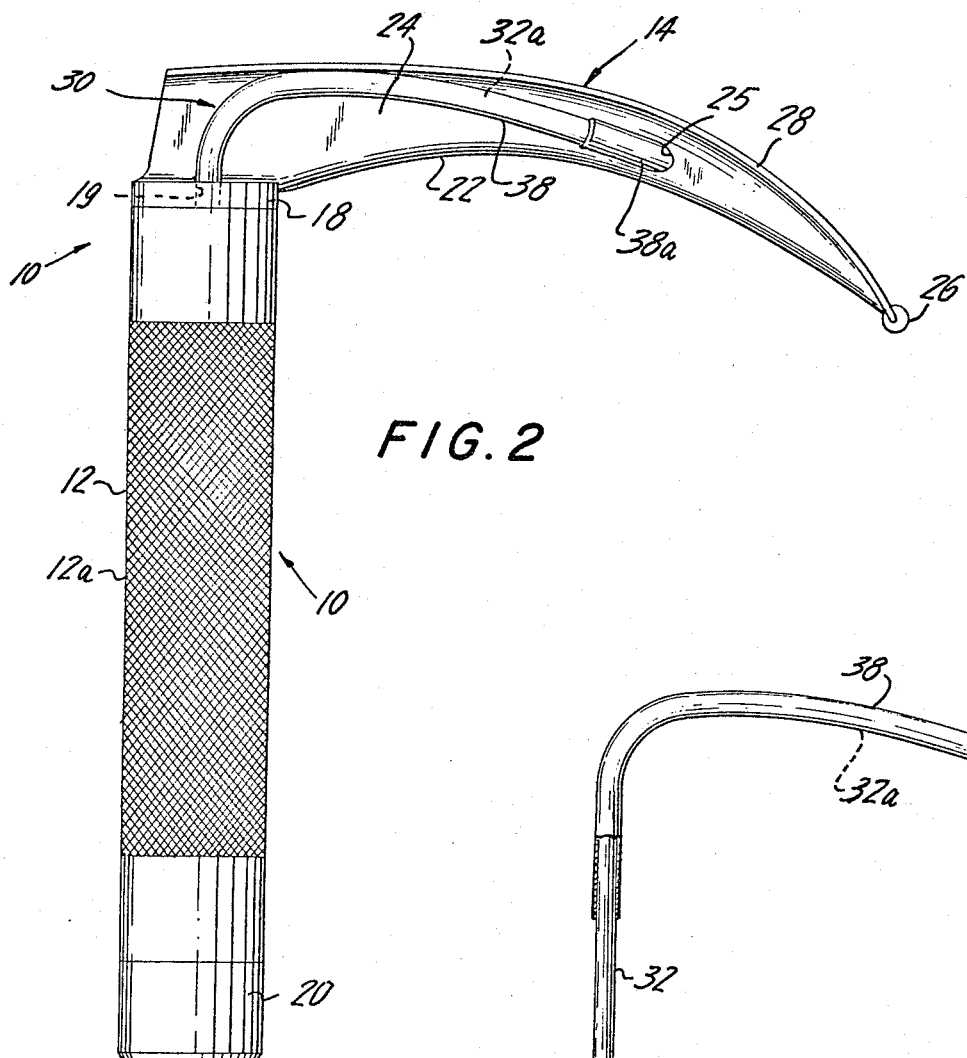
FIG. 2 is an elevational view of the other side of the autoclavable laryngoscope shown in FIG. 1.

Referring now to the accompanying Figures wherein like parts are represented by like numerals in the several views, there is shown an autoclavable laryngoscope in accordance with the invention and identified generally by the numeral 10. The laryngoscope 10 includes a hollow handle 12 and a blade 14 connected to handle 12 by means of conventional screw means 16 or by soldering or welding. However, it will be understood that the blade 14 and handle 12 may be integrally connected to provide a one piece or unitary structure as will be apparent to one skilled in the art.

Handle 12 is preferably formed of a metal such as brass or aluminum and is comprised of a hollow cylindrical casing 12a including a neck section 18, and a base section 20.

The neck section 18 includes an opening 19 therein (shown by the dotted lines in FIG. 2, the purpose of which will become apparent hereinafter). The base section 20 includes a depending sleeve 21 connected thereto(best shown in FIGS. 1, 1A, 1B and 4), the passageway 21a of which communicates with the interior of base section 20 and the interior of the hollow cylindrical casing 12a, for purposes to be described below.

The blade 14 is normally formed of the same material as the handle 12 and includes a spatula portion 22, a flange portion 24 and a rounded tip 26. The flange portion 24 includes an opening 25 (the purpose of which will become apparent hereinafter) and is connected to one side edge of the spatula portion 22 and is disposed at right angles to the transverse axis thereof. A subflange portion 28 is formed on the outer edge of the flange portion 24, the transverse axis of the subflange portion 28 being substantially perpendicular to the plane of the flange portion 24 and parallel to the transverse axis of the spatula portion 22.

Figure 3:
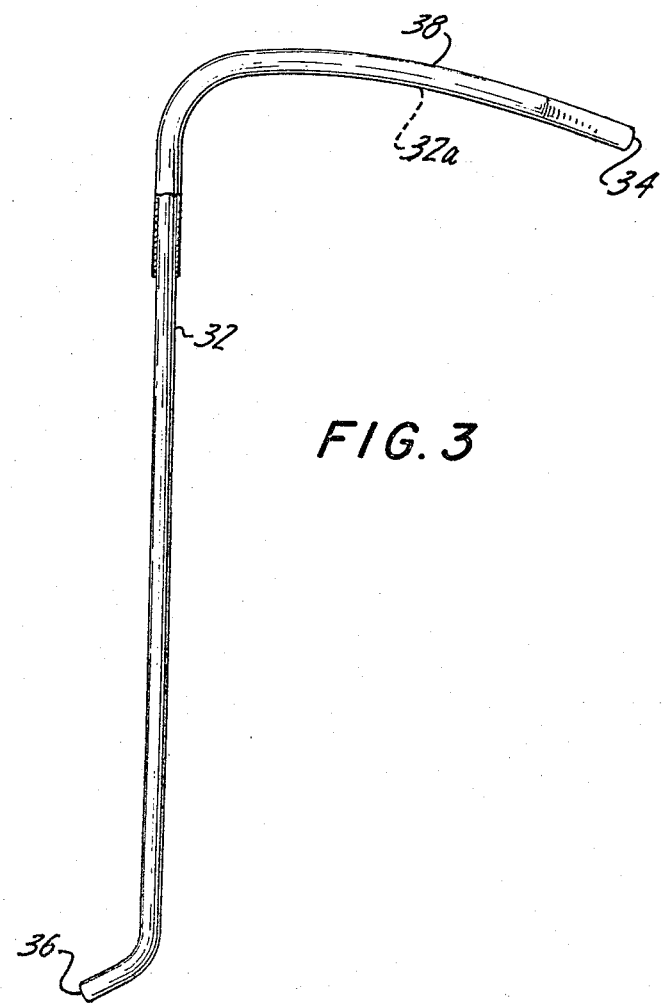
FIG. 3 is an elevational view of the illuminating means employed in the autoclavable laryngoscope shown in FIGS. 1 and 2.

The laryngoscope 10 includes illuminating means generally indicated by the numeral 30 and which is comprised of a sintered elongated glass rod 32, best shown in FIG. 3, formed from an oriented bundle of a plurality of individual optical fibers or filaments, preferably glass optical fibers or filaments. The rod 32 has a first optical face 34 and a second optical face 36 and further includes a portion 32a which is disposed in a protective tubular member 38 preferably formed of a metal such as brass, copper, aluminum, steel or other autoclavable materials.

As best seen in FIGS. 1 and 2, the illuminating means 30 is disposed in laryngoscope 10 so that the optical face 34 is received through sleeve 38a disposed in opening 25 of the flange portion 24 of blade 14. The portion 32a of rod 32 including the protective tubular member 38 enclosing the same extends from the opening 25 along the flange portion 24 of blade 14 and bends downwardly through opening 19 of neck section 18 of handle 12 into the cylindrical hollow casing 12a. The rod 32 continues on extending to the base section 20 and through the sleeve 21 and passageway 21a thereof so that the second optical face 36 thereof preferably terminates flush with the end of sleeve 21 (as shown best in FIGS. 4).

It will be appreciated that the portion 32a of glass rod 32 which is disposed externally to the handle 12 and beneath the subflange portion 28 will be protected by the protective tubular member 38 as well as by the subflange portion 28. The protective tubular member 38 will terminate below the neck section 18, although, if desired, may extend to the base section 20. In addition, the portion of protective tubular member disposed along the blade 14, may be bonded to the blade and/or the walls of opening 25 such as by soldering to ensure that the illuminating means 30 will be held securely in place.

The sintered elongated glass rod 32 in the form of a straight rod, by itself, forms no part of the present invention and may be purchased from American Optical Company or Mosaic Fabrication Company.

In forming the laryngoscope of the invention, the sintered elongated glass rod 32 is slipped into the protective tubular member 38 which fits tightly around portion 32a of glass rod 32. Both the glass rod 32 and the protective tubular member 38 are autoclavable and thus may be employed as illuminating means in substantially any autoclavable instrument in accordance with the present invention.

In order to bend the glass rod 32 including the protective tubular member 38 encasing the same, as shown in FIG. 3, to conform to the shape of the laryngoscope, the glass rod 32 and protective tubular member 38 are heated as by direct flame contact with said protective tubular member to soften the same. The glass rod 32 and protective tubular member 38 are bent into the desired shape and thereafter cooled by the ambient air.

The temperature at which the glass rod 32 and protective tubular member 38 are heated will normally be above the softening point of each of these materials but below the melting point thereof.

Furthermore, the lower end of the glass rod 32 will be bent, as by heating as described above, so that it will extend through the sleeve 21 depending from the base section 20 of handle 12.

The end faces of the glass rod are polished to form optical faces 34 and 36, optical face 36 being made flush with the end of sleeve 21.

Assemblage of the so-shaped glass rod 32 and protective tubular member 38 with the remaining components of the laryngoscope of the invention including the handle 12, blade portion 14, base section 20 and sleeves 38a and 21 can be carried by conventional techniques as will be apparent to one skilled in the art.

Figure 4:
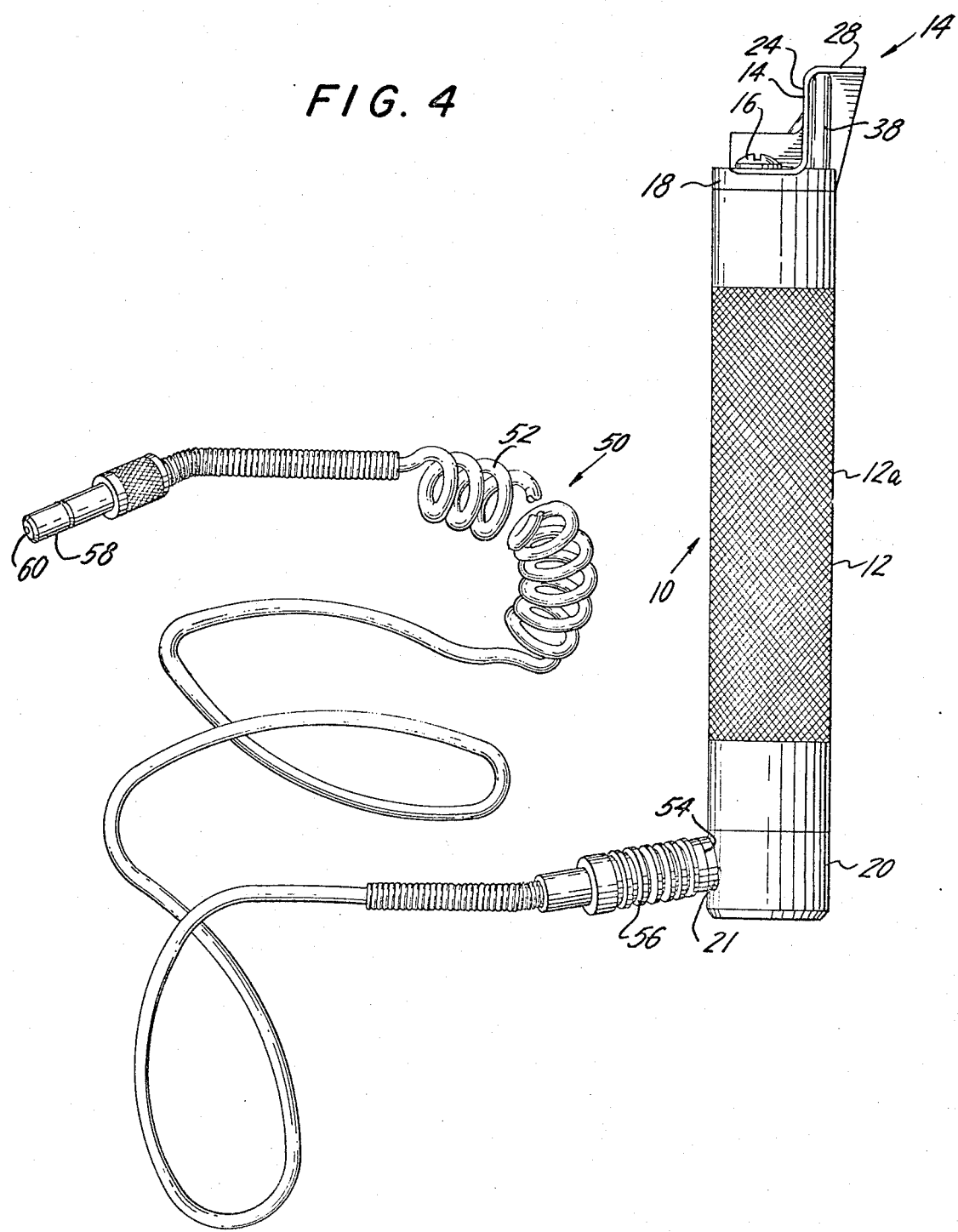
FIG. 4 is an rear view of the autoclavable instrument shown in FIGS. 1 and 2 wherein the laryngoscope is connected up to a second fiber optics bundle, said second bundle being adapted to be connected to a light source.

As indicated above, the sintered glass rod is formed from an oriented fiber optics bundle of individual glass fibers which fibers are coordinated from end to end. The optical face 36 of the glass rod 32 is adapted to be connected up with a second fiber optics bundle which usually will comprise an unoriented fiber optics bundle, which bundle is adapted to be connected up to a light source. In FIG. 4, there is shown a second fiber optics bundle 50 which is disposed within the sheathing 52. A first end 54 of the fiber optics bundle 50 including an optical face is securely disposed within the coupling member 56. The coupling member 56 will comprise a sleeve which is adapted to fit over and be secured to the sleeve 21 of the handle 12 of the laryngoscope described above so that the optical face 36 of the glass rod 32 will be in flush face-to-face engagement with the optical face disposed in the coupling member 56. The sleeve 21 will include externally disposed gripping members 23 which are adapted to grip the inside walls of the coupling member 56 so as to retain such coupling member in firm contact with the sleeve 21.

Furthermore, as shown in FIGS. 1A and 1B, the sleeve 21 will preferably be disposed at an angle A to the horizontal (as shown in FIG. 1A) of within the range of from about 10° to about 20° and preferably about 15°, and canted away from the blade 14 at an angle B to a horizontal line lying perpendicular to the plane of the blade (as shown in FIG. 1B) of within the range of from about 25° to about 45° and preferably about 30°. The coupling member 56 of the second fiber optics bundle 50 may therefore be connected up to the sleeve 21 and still not interfere with a physician using the laryngoscope.

The second fiber optics bundle 50 will preferably be in the form of an extensible-retractable helically coiled bundle as disclosed in U.S. Pat. No. 3,817,595 (the disclosure of which is incorporated herein by reference) at least seven feet in length and wherein the coiled area will comprise at least about ½ and preferably at least about ¾ or more of the bundle and will have a thickness within the range of from about 0.090 to about 0.150 inch.

It will now be appreciated that the second fiber optics bundle 50 is preferably in the form of the extensible-retractable helically coiled bundle and is disposed at the angles A and B to the handle and blade of the laryngoscope, so that the laryngoscope may be easily manipulated without interference from the bundle 50 and with only a minimum of torque and drag due to such bundle.

The other end of the fiber optics bundle 50 will include connecting means 58 which are adapted to connect up the other end face 60 of the fiber optics bundle 50 to a light source (as described above and not shown for drawing clarity) so as to complete a light path from the light source through the fiber optics bundle 50 through the optical face 36 of glass rod 32 through glass rod 32 and to the optical face 34.

It has been found that the connection of the oriented glass rod 32 via optical face 36 to the unoriented bundle 50 results in only a 20% loss in light. However, if the glass rod 32 were unoriented, the loss in light between the optical face 36 thereof and the fiber optics bundle 50 would be 50% or more. In such case, where the glass rod employed is comprised of an unoriented fiber optics bundle, the second fiber optics bundle 50 would have to be substantially thicker than that employed with the oriented glass rod 32 in order to make up for the 30% loss in light at the connection between the fiber optics bundle 50 and the unoriented glass rod 32.

The illuminating means employed in conjunction with the autoclavable instruments including the laryngoscope of the invention provides at least 10 times and in many cases 10 to 20 times more illumination than conventional lamps or bulbs now employed. Accordingly, it is seen that the subject laryngoscope is substantially more effective in illuminating a diagnostic or anesthesia-related field than laryngoscopes which employ lamps or bulbs as the illumination means therefor.

What is claimed is:

1. A method for making an autoclavable instrument having a handle portion and a working portion and a fiber optics element as illuminating means therefor, which comprises, providing an autoclavable sintered elongated glass rod comprising a sintered fiber optics bundle formed from a plurality of glass fibers sintered together to form a integral rod, said rod including first and second optical faces, disposing said first optical face of said glass rod in said working portion to provide illumination therefor, and disposing said second optical face of said glass rod in said handle portion for connection to a light source located externally of said instrument, said second optical face being disposed adjacent the end of said handle portion remote from said working portion.

2. The method in accordance with claim 1 including the step of inserting at least a portion of said sintered elongated glass rod in an autoclavable protective tubular member, and disposing said glass rod in said autoclavable instrument so that portions of said glass rod which are externally exposed with respect to said instrument other than said optical faces, are protected by said protective tubular member.

3. The method in accordance with claim 1 wherein said glass rod is formed from an oriented fiber optics bundle.

4. The method in accordance with claim 2 including the steps of heating at least a portion of said glass rod protected by said protective tubular member to a temperature sufficiently high to soften but not melt said portion of said glass rod and protective tubular member disposed thereon, bending said glass rod and protective tubular member into a predetermined desired shape to fit the shape of a particular instrument, cooling said glass rod and protective tubular member, and thereafter inserting said glass rod in said autoclavable instrument so that said glass rod and said protective tubular member substantially follows the contours of said instrument.

5. The method in accordance with claim 1 further including the step of connecting said second optical face to a second fiber optics bundle adapted to be operatively connected to a light source so as to complete a light path from said first optical face to said light source.

* * * * *